United States Patent [19]

Stauffer

[11] Patent Number: 5,557,001
[45] Date of Patent: Sep. 17, 1996

[54] SILICONE MONOMER PROCESS

[76] Inventor: John E. Stauffer, 6 Pecksland Rd., Greenwich, Conn. 06831

[21] Appl. No.: 434,606

[22] Filed: May 4, 1995

[51] Int. Cl.⁶ .................... C07F 7/08; C07F 7/18
[52] U.S. Cl. .................................................. 556/470
[58] Field of Search ............................... 556/470

[56] References Cited

U.S. PATENT DOCUMENTS

| | | | |
|---|---|---|---|
| 2,698,861 | 1/1955 | Shorr | 556/470 |
| 2,831,011 | 4/1958 | Sommer | 556/470 |
| 3,069,451 | 12/1962 | Fritz | 556/470 |

OTHER PUBLICATIONS

Bazant et al., *Organosilicon Compounds*, vol. 2, Part 1, Academic Press, New York 1965, pp. 109 and 307.

*Primary Examiner*—Paul F. Shaver
*Attorney, Agent, or Firm*—Young & Basile, P.C.

[57] ABSTRACT

The invention concerns a process of preparing silicone monomer products comprising a reaction between alkylchloro silane and an aliphatic ether in the presence of a catalyst to form the corresponding alkoxyalkyl silane silicone monomer product and alkyl chloride that are subsequently separated.

6 Claims, 1 Drawing Sheet

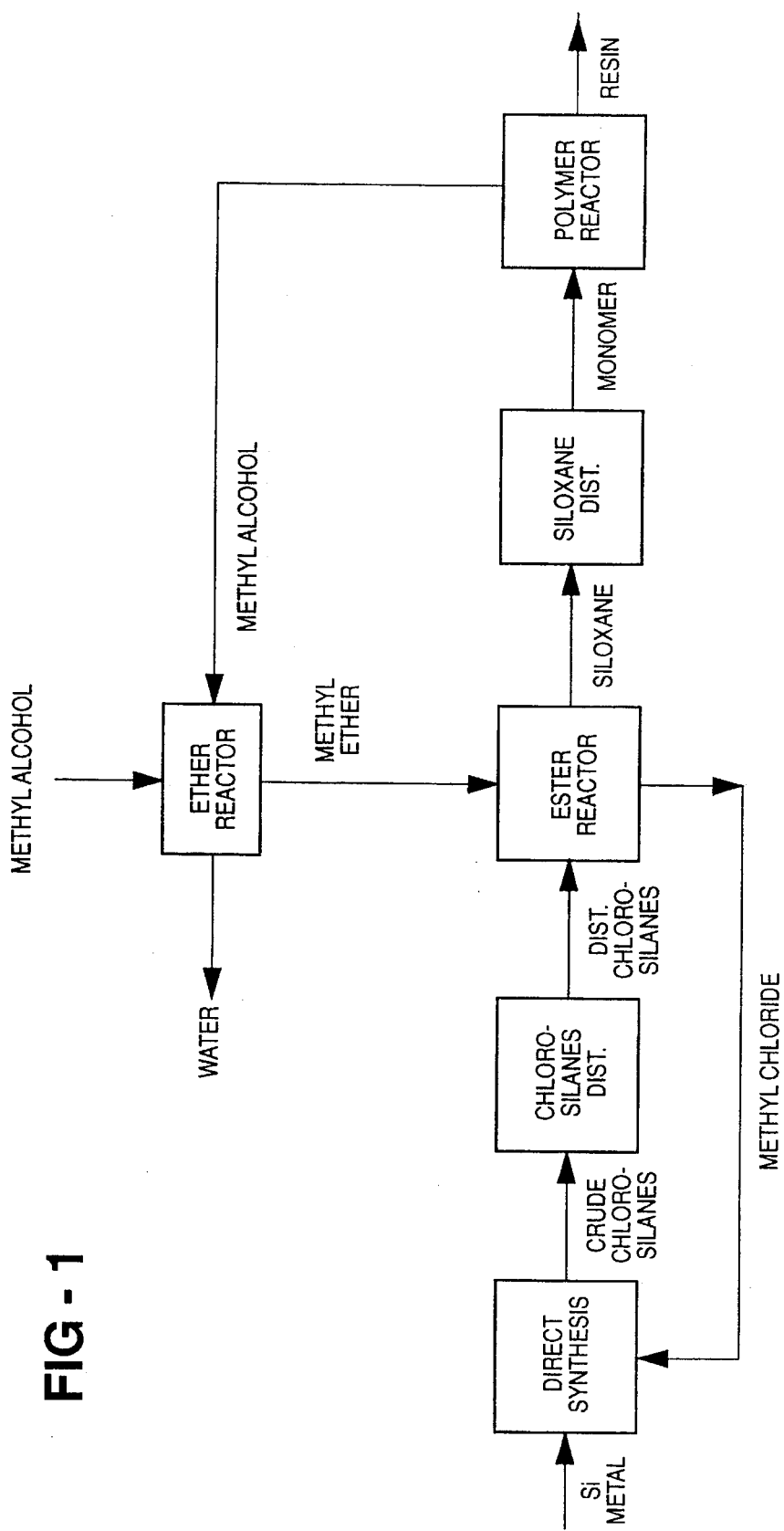

SILICONE MONOMER PROCESS

FIELD OF THE INVENTION

A process is provided for the preparation of alkoxyalkyl silanes including the compounds dimethoxydimethyl silane, methoxytrimethyl silane, and trimethoxymethyl silane. These compounds have proven to be useful monomers in the preparation of silicone resins. The process comprises the reaction of an alkylchloro silane with an aliphatic ether to produce the corresponding ester and alkyl chloride. By carrying out this conversion under essentially anhydrous conditions, the formation of hydrogen chloride is avoided and high yields of ester monomer products are obtained.

BACKGROUND OF THE INVENTION

The standard method of preparing monomers for the production of methyl silicone resins involves the following steps:

Methyl chloride is reacted with finely divided silicon and a copper catalyst at around 300° C. to produce chloromethyl silanes. This reaction is known as the direct synthesis or Rochow synthesis, named after the chemist who discovered the process.

Next the chloromethyl silanes are fractionated by distillation to purify the desired intermediates.

The separated chloromethyl silanes are hydrolyzed with water to produce condensation products and byproduct hydrochloric acid.

The oligomers produced in the hydrolysis step are further purified by distillation. For example, dichlorodimethyl silane on hydrolysis forms the cyclic tetramer with a boiling point of 175° C. The monofunctional compound chlorotrimethyl silane on hydrolysis forms hexamethyldisiloxane.

Finally, the purified oligomers are polymerized to the desired resins.

Although the above scheme represents a great improvement over earlier routes involving the use of Grignard reagents, there are fundamental drawbacks with the technology. First, purification of the chloromethyl silanes is difficult because trichloromethyl silane boils only 4° C. lower than dichlorodimethyl silane. Distillation columns with up to 200 trays are required and even then reflux ratios approaching 100:1 are needed to obtain the desired purities.

Furthermore, the hydrolysis step, while using straightforward chemistry, is troublesome in execution. A highly corrosive byproduct, hydrochloric acid, is formed in the conversion. Expensive materials of construction are therefore necessary. Also, this waste acid stream must be treated or other means must be found to dispose of this byproduct.

The condensation products from the hydrolysis step likewise present challenges. Invariably, sludges are formed which reduce yields and make the purification of the cyclics more difficult. The cyclics distillation step requires a significant capital expenditure and adds considerably to the cost of utilities.

In order to circumvent the shortcomings of existing technology, numerous proposals have been made to prepare the methoxy derivatives from the chloromethyl silanes produced in the direct synthesis. The rationale for this approach is that the methoxy compounds are easier to separate than the chloro compounds. Moreover, the methoxymethyl silanes are excellent monomers for silicone resins; they readily polymerize to produce the desired high molecular weight polymers required in this application.

Accordingly, the hydrolysis step in the standard synthesis is replaced by a methanolysis reaction. Thus, chloromethyl silane is reacted with methyl alcohol to form methoxymethyl silane and hydrogen chloride. In some proposals methyl chloride instead of hydrogen chloride is formed. Regardless of the reaction conditions, however, it is almost impossible to prevent the formation of some hydrogen chloride. Furthermore this acid reacts with the methanol to form water which in turn reacts with chloromethyl silane to produce more hydrogen chloride. Immediately some of the silanes condense to form sludges.

To get around these difficulties, various suggestions have been made. Complicated arrangements for adding one reactant to the other have been outlined. Another approach is to employ a hydrogen chloride receptor. For example, ammonia and various amines have been mentioned for this use. Additional methods include blowing dry air or nitrogen through the reaction mixture, the use of vacuum, or the use of refluxing solvents. Because of the sensitivity of silanes to hydrolysis, however, none of the above proposals have proven to be entirely satisfactory.

Therefore, it is an object of the present invention to provide a silicone monomer process which overcomes the disadvantages of existing processes. It is an object to provide for the efficient separation of monomers in the required purities. A further object is to avoid the production of hydrogen chloride. Still another object is to produce monomers of the needed functionality such that they can be readily polymerized to the desired silicone resins.

These and other objectives, features and advantages of the invention will become apparent from the following description and the accompanying drawing FIG. 1.

BRIEF SUMMARY OF THE INVENTION

A process of preparing silicone monomers of the present invention comprises an esterification reaction between a chloroalkyl silane and an aliphatic ether to form the corresponding alkoxyalkyl silane and alkyl chloride. This reaction is conveniently carried out in the vapor phase using a suitable esterification catalyst to achieve favorable reaction kinetics. Essentially anhydrous conditions are maintained, thereby avoiding condensation reactions.

The esterification reaction is applicable to the preparation of dimethoxydimethyl silane from dichlorodimethyl silane and dimethyl ether. When reacting trichloromethyl silane with dimethyl ether, trimethoxymethyl silane is produced. In practice these and other methoxy silanes are produced in conjunction with each other and are subsequently separated by distillation.

Instead of using dimethyl ether, the esterification reaction can be run with diethyl ether. In this case the corresponding ethyl esters are produced. Furthermore, the reaction is amenable to converting chloroethyl silanes to their respective esters.

The esterification reaction of the present invention can be integrated into a silicone process that includes a direct synthesis step, distillation of the intermediate alkylchloro silanes, esterification of the alkylchloro silanes, distillation of resulting alkoxy silanes, and polymerization. The ether required for the esterification reaction can be produced from alcohol in a catalytic reactor. By recycling byproduct streams within the silicone process, the net effect is the production of silicone resins from silicon and alcohol with water as the only byproduct.

BRIEF DESCRIPTION OF THE DRAWING

The invention will be better understood by reference to the preferred embodiments illustrated in FIG. 1. The drawing is a block diagram of an integrated silicone process comprising the proprietary esterification step of the present invention.

DETAILED DESCRIPTION OF THE INVENTION

In a preferred aspect, the invention concerns a process of preparing silicone monomers comprising an esterification reaction between an alkylchloro silane and an aliphatic ether in the presence of an esterification catalyst to form the corresponding alkoxyalkyl silane monomer and alkyl chloride, according to the equation:

$$R_nSiCl_{4-n}+(4-n)R'OR' \rightarrow R_nSi(OR')_{4-n}+(4-n)R'Cl$$

where n=0,1,2 or 3 and R and R' independently represent methyl or ethyl radicals.

In the special case where the desired monomer is dimethoxydimethyl silane, the generalized equation reduces to:

$$Me_2SiCl_2+2MeOMe \rightarrow Me_2Si(OMe)_2+2MeCl$$

where Me stands for the methyl radical.

The significance of the above reaction is that it can be carried out under essentially anhydrous conditions. This result is important for several reasons. First, without any moisture present, neither the chloro silanes nor the resulting esters can be condensed to form oligomers and sludges of various compositions. Thus, yields of product are maximized and further purification of the monomers is facilitated. Second, in the absence of hydrochloric acid, the selection of materials of construction is simplified. Corrosion resistant materials are not obligatory. Third, there is no waste hydrogen chloride to treat or otherwise dispose of. And fourth, byproduct alkyl chloride can be easily recovered and recycled to the direct synthesis step.

Perhaps most significant about the monomer process is the fact that the stream mixed esters produced by the esterification reaction can be readily purified by distillation. This possibility is most clearly demonstrated by the following table which shows the boiling points for various monomers.

| Chloro Silane | Boiling Pt., °C. | Methoxy Silane | Boiling Pt., °C. |
|---|---|---|---|
| Me$_3$SiCl | 57.3 | Me$_3$SiOMe | 56.5 |
| Me$_2$SiCl$_2$ | 70.0 | Me$_2$Si(OMe)$_2$ | 80.5 |
| MeSiCl$_3$ | 65.7 | MeSi(OMe)$_3$ | 103.5 |
| SiCl$_4$ | 57.6 | Si(OMe)$_4$ | 121–122 |

From this table, it is apparent that instead of a difference of about 4° C. between the boiling points of dichlorodimethyl silane and trichloromethyl silane, there is a spread of 23° C. between the boiling points of dimethoxydimethyl silane and trimethoxymethyl silane to utilize. This increase makes all the difference in separating these monomers.

The importance of obtaining monomers in high purity cannot be underestimated. Many silicone products require the preparation of polymers of very high molecular weight ranging from 2,000,000 to 5,000,000. In order to achieve these results, the purity of the difunctional monomer must exceed 99.99 percent. Excessive contamination with trifunctional silanes causes branch chains and even cross linking. Of equal concern, impurities of monofunctional compounds lead to the termination of chains.

The features of the present invention will be better understood by referring to the block diagram in FIG. 1. In the direct synthesis, silicon metal is reacted with methyl chloride to produce a crude product stream of chlorosilanes. This stream is fractionated to remove the low and high boiling ends. The distilled chlorosilanes are fed to the esterification reactor where they are converted with ether to siloxanes and byproduct methyl chloride. The latter is recycled to the direct synthesis unit. The mixed siloxanes are distilled to produce pure monomers. As indicated above, the significant differences in the boiling points of the various siloxanes facilitate their separation. Finally, the purified monomers blended in the correct proportions are polymerized to silicone resin. The alcohol, e.g., methyl alcohol, or as the case may be, ethyl alcohol alcohol split out in the polymerization reaction is recycled to a reactor that generates ether.

In order to better appreciate the chemistry of the esterification reaction, both the thermodynamics and kinetics of this reaction should be considered. First, looking at the thermodynamics, it is important to keep in mind that the free energy change is independent of the reaction paths taken. Thus, the esterification reaction can be replaced by a series of separate reactions each of which is well understood. For the special case of producing the monomer dimethoxydimethyl silane, the reactions of interest are:

1. $2MeOMe + 2H_2O \xrightleftharpoons{cat.} 4MeOH$

2. $Me_2SiCl_2 + 2MeOH \longrightarrow Me_2Si(OMe)_2 + 2HCl$

3. $2MeOH + 2HCl \xrightleftharpoons{cat.} 2MeCl + 2H_2O$

Combining the above equations, the following equation is obtained:

$$4Me_2SiCl_2+2\ MeOMe \rightarrow Me_2Si(OMe)_2+2\ MeCl$$

The latter equation is recognized as the esterification reaction of the present invention. The thermodynamics for this reaction is the same as for the combined reactions represented by equations 1,2 and 3. It should be noted that equations 1 and 3 are reversible under the conditions assumed, namely, one atmospheric pressure and temperatures in the range of 25° to 275° C. Equation 2 is a variation of Von Ebelman's classic synthesis for silicon esters. It goes to completion, however, under the same conditions. Thus, the overall reaction 4 is driven to completion, which is one way of saying that the thermodynamics for the esterification reaction is favorable.

The mechanism of the esterification reaction cannot be assumed to be the same as indicated by equations 1,2 and 3. The reason, of course, is that the esterification reaction is carried out under essentially anhydrous conditions whereas water is shown to be a reactant in both reactions 1 and 3. Nevertheless, the separate reactions are of value in providing some clues to reaction kinetics.

Inasmuch as the chemical bonds which are broken or formed in the esterification reaction also undergo cleavage in reactions 1,2 and 3, the catalysts indicated for equations 1 and 3 are of interest. Among the catalysts known to promote reaction 1 are aluminum oxide and sulfuric acid. Reaction 3 is promoted also by aluminum oxide as well as by salts of copper and zinc.

Thus, a catalyst of choice to promote the esterification reaction is aluminum oxide. Alternative catalysts are described in an article titled, "Solid Superacid Catalysts" by M. Misono and T. Okuhara, *Chemtech*, November 1993, pages 23–29. This paper provides an excellent survey of catalysts with extraordinary acid strengths that have been found to be effective substitutes in processes based on sulfuric acid, HF, and $AlCl_3$. One superacid of particular interest is the complex $AlCl_3$—$CuCl_2$ as it contains copper which is a known catalyst for both reaction 3 and for the direct synthesis. Because ethers are recognized to be relatively unreactive, the esterification reaction of the present invention is dependent on the selection of such a suitable catalyst in order to achieve favorable reaction rates.

In another preferred aspect, the invention concerns an alkoxyalkyl silane having the formula $R_nSi(OR')_{4-n}$ where n is 1,2 or 3 and R and R' independently represent a methyl or ethyl radical, produced by the process of the invention.

Silicone resins have attained an important status in world commerce. These materials are vital to innumerable applications. Any manufacturing improvements that are capable of reducing the cost of these materials or improving their performance would be significant. The present invention, by offering solutions to serious shortcomings in existing silicone resin technology, promises to make positive contributions to the art.

The embodiments of the invention in which exclusive property or privilege is claimed are defined as follows:

What is claimed is:

1. A process of preparing silicone monomers comprising a reaction between an alkylchloro silane and an aliphatic ether in the presence of a catalyst to form the corresponding alkoxyalkyl silane monomer and alkyl chloride.

2. A process according to claim 1 in which the alkylchloro silane is dichlorodimethyl silane, the aliphatic ether is dimethyl ether, the alkoxyalkyl silane is dimethoxydimethyl silane, and the alkyl chloride is methyl chloride.

3. A process according to claim 1 in which the alkylchloro silane is dichlorodiethyl silane, the aliphatic ether is diethyl ether, the alkoxyalkyl silane is diethoxydiethyl silane, and the alkyl chloride is ethyl chloride.

4. A process according to claim 1 in which the catalyst is selected from the group consisting of aluminum oxide and $AlCl_3$—$CuCl_2$.

5. A process according to claim 4 in which the catalyst is aluminum oxide.

6. A process according to claim 4 in which the catalyst is $AlCl_3$—$CuCl_2$.

* * * * *